United States Patent [19]

Choudhary et al.

[11] Patent Number: 5,306,854

[45] Date of Patent: Apr. 26, 1994

[54] TWO STEP PROCESS FOR PRODUCTION OF LIQUID HYDROCARBONS FROM NATURAL GAS

[75] Inventors: Vasant R. Choudhary; Subhash D. Sansare; Amarjeet M. Rajput, all of Pune, India

[73] Assignee: Council of Scientific & Industrial Research, New Delhi, India

[21] Appl. No.: 911,448

[22] Filed: Jul. 10, 1992

[51] Int. Cl.$^5$ ................................. C07C 2/00
[52] U.S. Cl. ........................ 585/315; 585/407; 585/415; 585/652; 585/943
[58] Field of Search .............. 585/652, 407, 415, 943, 585/315

[56] References Cited

U.S. PATENT DOCUMENTS

| | | | |
|---|---|---|---|
| 4,608,449 | 8/1986 | Baerns et al. | 585/652 |
| 4,754,091 | 6/1988 | Jezl et al. | 585/415 |
| 4,754,093 | 6/1988 | Jezl et al. | 585/415 |
| 4,814,539 | 3/1989 | Jezl et al. | 585/415 |
| 4,891,457 | 1/1990 | Owen et al. | 585/415 |
| 5,004,852 | 4/1991 | Harandi | 585/415 |
| 5,068,486 | 11/1991 | Han et al. | 585/652 |
| 5,087,787 | 2/1992 | Kimble et al. | 585/415 |

*Primary Examiner*—Asok Pal
*Attorney, Agent, or Firm*—Pennie & Edmonds

[57] ABSTRACT

The invention discloses a two step process for conversion of natural gas to liquid hydrocarbons of gasoline range comprising oxidation pyrolysis of natural gas olefins containing gaseous products in the first stage and conversion of the olefins, formed in the first step, without separating them from the gaseous product stream to liquid hydrocarbons of gasoline range in the second step. The process of the invention could be used in petrolium industries for producing gasoline liquid hydrocarbon fuels and aromatic hydrocarbons. The present invention is commercially viable and energy efficient.

10 Claims, No Drawings

TWO STEP PROCESS FOR PRODUCTION OF LIQUID HYDROCARBONS FROM NATURAL GAS

This invention relates to a novel two-step process for the production of liquid hydrocarbons from natural gas. This invention particularly relates to a novel two-stage process comprising oxidative pyrolysis of natural gas olefins (mostly ethylene, propylene and butylenes) containing gaseous products in the first stage and conversion of the olefins, formed in the first step, without separating them from the gaseous product stream, to liquid hydrocarbons of gasoline range in the second step, for the production of gasoline range hydrocarbons from natural gas. The process of the present invention could be used in petroleum industries for producing gasoline liquid hydrocarbon fuels and aromatic hydrocarbons.

World reserves of natural gas are constantly being upgraded and more natural gas being discovered than oil. Natural gas typically comprises a major amount of methane and ethane and minor amounts of propane, butanes, pentanes, $CO_2$ and nitrogen. Natural gas is used principally as a source of heat in commercial, industrial and residential service. In chemical industries, natural gas is used mainly as a source of hydrogen for fertilizer industries and syn-gas (CO and $H_2$) for production of methanol and in the Fischer-Tropsch synthesis. The conventional processes, which involve $C_1$-chemistry for the production of methanol, aliphatic hydrocarbons and oxygenated hydrocarbons from natural gas require the intermediate formation of synthesis gas. The processes suffer from the requirement of complicated engineering steps and also from the relative inefficiency of carrying out extensive oxidation of natural gas to carbon monoxide and then reduction of carbon monoxide to methanol or aliphatics and oxygen containing compounds.

Because of the problems associated with transportation of a very large volumes of natural gas, most of the natural gas produced, particularly at remote places, is flared and hence wasted. If efficient technology were available for the conversion of natural gas to easily transportable and value added products like liquid hydrocarbons, this can have far reaching economic impact and the exploration of more gas-rich fields could greatly increase the natural-gas reserves.

Earlier processes for conversion of natural gas into liquid hydrocarbons are based on the conversion of syn-gas, obtained from natural gas, to aliphatic hydrocarbons or oxygenated hydrocarbons by the well known Fischer-Tropsch synthesis and to methanol which is further converted to liquid hydrocarbons by Mobil's MTG (methanol-to-gasoline) process [P. W. Alpin. Chem. Eng. Aust. 7-13, (1986). C. J. Maiden, Chemtech 18(1), 38, 42 (1988)]. The conversion of natural gas to liquid hydrocarbons by both the Fischer-Tropsche and methanol routes are more or less established technology. Both the Fischer-Tropsch route and the methanol route for conversion of natural gas to higher hydrocarbons require the primary conversion of natural gas to synthesis gas (carbon monoxide and hydrogen) as the first step, then the syn-gas is converted in the second step to aliphatic hydrocarbons in the Fischer-Tropsch synthesis or to methanol which is further converted in the next step to liquid hydrocarbons in the MTG process. These processes suffer from the requirement of complicated engineering steps and also from the relative inefficiency of carrying out extensive oxidation of natural gas to carbon monoxide and then reduction of carbon monoxide to aliphatic hydrocarbons in the Fischer-Tropsch synthesis or to methanol in the MTG process.

The main object of the present invention is to provide a novel two-step process, which is commercially viable and energy saving, for the production of gasoline range hydrocarbons from natural gas by carrying out oxidative conversion of natural gas to olefines containing products in the first step and then conversion of the olefins from the product stream of the first step, without their separation, to liquid hydrocarbons of gasoline range in the second step, using the product stream of the first step as a feed.

In the prior art, a two-step process for conversion of natural gas to liquid hydrocarbons involving oxidative conversion of natural gas to olefins containing gaseous products in the first step and then conversion of the olefines formed in the first step, without their separation, to liquid hydrocarbons of gasoline range in the second step using the product stream of the first step as a feed has not been reported so far.

The main finding of the present invention is that natural gas can be converted to gasoline range hydrocarbons (to $C_5$ to $C_{10}$ hydrocarbons) in high yields in an energy efficient manner by carrying out the conversion of natural gas in the following two consecutive steps:

Step I

Oxidative conversion of natural gas to ethylene and minor amounts of $C_3$ and $C_4$ olefins by reacting natural gas with free-oxygen at or close to atmospheric pressure in absence of any catalyst.

Step II

Conversion of the ethylene and higher olefine formed in the Step I to liquid hydrocarbons of gasoline range over acidic catalyst containing high silica pentasil zeolite, using product stream of the Step-I as a feed.

Accordingly, the present invention provides a novel two-step process for the conversion of natural gas to liquid hydrocarbons of gasoline range.

The first step of the said two-step process comprises passing continuously natural gas and oxygen (or air), along with steam through an empty tubular reactor at a pressure in the range of 0.5-3 atmospheres, temperature in the range of 600°-1100° C., $O_2$/natural gas ratio of 0.0001-0.5, steam/natural gas ratio of 0.001-10 and gas hourly space velocity (GHSV) of 200-50,000 $h^{-1}$ and separating the water from the product stream by known methods.

For the first step of the said two-step process, the preferred pressure range may be 1 to 2 atmospheres, the preferred temperature range may be 650° to 1000° C., the preferred $O_2$/natural gas ratio range may be 0.003 to 0.3, the preferred steam/natural gas ratio range may be 0.01 to 5 and the preferred gas hourly space velocity range may be 300 to 30,000 $h^{-1}$.

The products formed in the first step of the said two step process are ethylene, carbon monoxide, carbon dioxide, small amounts of propylene, butylenes and hydrogen and also trancess of higher hydrocarbons. The product stream obtained from the first step comprises $C_2$–$C_4$ olefins (i.e. ethylene, propylene and butylenes), methane, ethane, CO, $CO_2$, small amounts of propane, butanes, oxygen and hydrogen and tracers of higher hydrocarbons. The process of preparing $C_2$–$C_4$ olefins, particularly ethylene by oxidative cracking of ethane in a similar manner as of the Step I described above has been made the subject matter of our co-pending application No. 715/DEL/90 filed Jul. 13, 1990 at the Patent Office of India.

The second step of the said two-step process comprises passing continuously the product stream of the first step of the said two-step process over a known solid acid catalyst containing high silica pentasil zeolite having channel diameter of 5-6 A° in a fixed bed reactor at a pressure in the range of 1-50 atmospheres, temperature in the range of 250°-700° C. and a gas hourly space velocity in the range of 100-50,000 $h^{-1}$, separating the liquid hydrocarbons, $C_3$-$C_4$ hydrocarbons (or liquified petroleum gas i.e. LPG) and oxides of carbon by known manners and if required, recycling the $C_1$-$C_2$ or $C_1$-$C_4$ hydrocarbons and oxygen to the first step.

For the second step of the said two-step process, the preferred pressure range may be 1 to 30 atmospheres, the preferred temperature range may be 300° to 600° C. and preferred gas hourly space velocity range may be 250 to 25,000 $h^{-1}$.

The products formed in the second step of the said two-step process of the invention are liquid hydrocarbons of gasoline range (i.e. $C_5$-$C_{10}$ hydrocarbons), $C_3$-$C_4$ hydrocarbons (or LPG) and small amounts of methane and ethane.

The present invention reveals that natural gas can be converted to liquid hydrocarbons of gasoline range in high yields by the said two-step process described above.

In the first step of the said two-step process of the invention the conversion of carbon in natural gas as high as 20-25% with 80-95% selectivity for ethylene, based on carbon balance, in the oxidative conversion of natural gas to ethylene could be achieved.

In the second step of the said two-step process of the invention, ethylene at concentration as low as 2-10 mol % in the feed stream could be converted almost completely in the present of CO, $CO_2$, $O_2$ and $CH_4$, giving yield for liquid hydrocarbons of gasoline-range as high as 70% or above.

The present invention is described with respect to the following examples. These are provided for illustrative purpose only and are not to be construed as limitation on the invention.

DEFINATIONS OF TERMS USED IN THE EXAMPLES

Conversion of natural gas in the first step of the said process is given in terms of percentage of carbon in natural gas converted to carbon containing products viz. ethylene, CO and $CO_2$, etc.

Selectivity for ethylene in the first step of the said process is obtained from the conversion of carbon in natural gas to ethylene and the total conversion of carbon in natural gas to carbon containing products, as follows.

Selectivity for ethylene (%) =

$$\left[ \frac{\text{Conversion of carbon to ethylene (\%)}}{\text{Total conversion of carbon (\%)}} \right] \times 100$$

Gas Hourly Space Velocity (GHSV) is the volume of feed gases (measured at STP) passed through a unit volume of reactor or catalyst per hour.

Total conversion of ethylene in the second step of the said process is obtained as follows:

Total conversion of ethylene (%) =

$$\left\{ \frac{[\text{ethylene in hydrocarbon feed (wt \%)}] - [\text{ethylene in hydrocarbon products (wt \%)}]}{[\text{ethylene in hydrocarbon feed (wt \%)}]} \right\}$$

Selectivity for different products in the second step of the said process is obtained from the conversion of ethylene to a particular product and the total conversion of ethylene, as follows Selectivity for a particular product (%) =

$$\frac{[\text{Conversion of ethylene to a particular product (\%)}]}{[\text{Total conversion of ethylene (\%)}]} \times 100$$

The product concentrations are expressed in mole %. Conversion given in the examples is per pass conversion.

EXAMPLE 1

Conversion of natura gas to liquid hydrocarbons has been carried out in the following two steps.

Step-I: Oxidative Conversion of Natural Gas to Ethylene and Other Lower Olefins.

A mixture of natural gas, oxygen and steam was passed through an empty tubular reactor (internal diameter: 1.4 cm and reactor volume: 7.5 cm$^3$) made of quartz at the following process conditions.

| | |
|---|---|
| Temperature: | 955° C. |
| Pressure: | 1.05 atm. |
| $O_2$/natural gas ratio: | 0.05 |
| Steam/natural gas ratio: | 2.2 |
| Gas hourly space velocity (GHSV): | 4650 |

The reaction temperature was measured by a Chromel-Alumel thermocouple located at the centre of the reaction zone in the reactor. The products coming out from the reactor were cooled by passing them through a water condenser and the water vapours from the product stream were removed by their condensation. The gaseous products were analysed using a gas chromatograph with a thermal conductivity detector.

The reslults obtained were as follows:

The conversion of carbon in the natural gas to ethylene and oxides of carbon was 20.8% with a selectivity for ethylene of 95.1%. The composition of the gaseous product stream after removal of water vapours, was 0.9% ethylene, 1.7% ethane, 73.0% methane, 0.6% propylene, 0.2% butenes, 0.7% propane, 0.1% butanes, 2.5% $CO_2$, 0.8% CO and balance $N_2$, $H_2$ and $O_2$ etc.

Step-II: Catalytic Conversion of Ethylene and Other Olefins from the Product Stream of Step-I to Liquid Hydrocarbons.

The product stream of the step-I, after removal of water by condensation, was passed over Pt.H-ZSM-5.$Al_2O_3$ (0.1 wt % Pt and 50 Wt % $Al_2O_3$) catalyst in the form of 1/16" extrudes packed in a fixed bed stainless steel reactor (internal diameter: 1.5 cm and reactor volume: 20 cm$^3$) at the following process conditions.

| | |
|---|---|
| Temperature: | 402° C. |
| Pressure: | 11.5 atm |

| | |
|---|---|
| Gas Hourly Space Velocity (GHSV): | 2050 h$^{-1}$ |

The reaction temperature was measured by a Chromel-Alumel thermocouple located in the centre of the catalyst bed. After 1 hour of start of the reaction analysis of the products was done using an on-line gas chromatograph. For this pourpose the product stream, after reduction of the pressure, was passed through a heated gas sampling valve connected to the gas chromatograph. All the connecting lines to gas chromatographs were heated for avoiding the condensation of products in the lines. The product stream coming out from the gas sampling valve was cooled using a chilled water condenser and the condensed liquid products (i.e. liquid hydrocarbons) were collected. The gases products were measured by a gas meter and analysed by the gas chromatograph. The results obtained were as follows:

| | |
|---|---|
| Total conversion of ethylene: | 95.6% |
| Selectivity for liquid hydrocarbons (C$_{5+}$-hydrocarbons): | 71.5% |
| Selectivity for C$_3$ + C$_4$ hydrocarbons: | 28.0% |

Distribution of Liquid Hydrocarbons

| | |
|---|---|
| C$_5$–C$_8$ Paraffins: | 3.4 wt. % |
| C$_6$–C$_8$ Aromatics: | 55.0 wt. % |
| C$_9$ & C$_{10}$ Hydrocarbons: | 41.6 wt. % |

EXAMPLE 2

The conversion of natural gas into liquid hydrocarbons in the two step was carried out by the procedures described in Example-1 at the following process conditions.

| Process Conditions Employed in Step-I. | |
|---|---|
| Temperature: | 897° C. |
| Pressure: | 0.95 atm. |
| O$_2$/natural gas ratio: | 0.13 |
| Steam/natural gas ratio: | 4.83 |
| Gas hourly space velocity (GHSV): | 3850 h$^{-1}$ |

The results obtained were as follows: The conversion of carbon in the natural gas to ethylene and oxides of carbon was 20.2% with a selectivity for ethylene of 93.8%. The composition of the gaseous product stream, after removal of water vapours, was ethylene 8.9%, ethane 2.5%, methane, 66.7%, propylene 0.7%, butenes 0.1%, propane 0.2%, butanes 0.05%, CO$_2$ 2.3%, CO 0.9% and balance N$_2$, H$_2$ and O$_2$ etc.

| Process Conditions Employed in Step-II | |
|---|---|
| Temperature: | 500° C. |
| Pressure: | 14.5 atm |
| Gas Hourly Space Velocity (GHSV): | 1030 h$^{-1}$ |

The results obtained were as follows:

| | |
|---|---|
| Total conversion of ethylene: | 96.5% |
| Selectivity for liquid hydrocarbons: | 67.5% |
| Selectivity for C$_3$ + C$_4$ hydrocarbons: | 32.1% |

Distribution of Liquid Hydrocarbons

| | |
|---|---|
| C$_5$–C$_8$ paraffins (wt. %): | 4.0 |
| C$_6$–C$_8$ aromatics (wt. %): | 80.1 |
| C$_9$ and C$_{10}$ hydrocarbons (wt. %): | 15.9 |

EXAMPLE 3

The conversion of natural gas into liquid hydrocarbons in thw two steps was carried out by the procedures described in Example-1 at the following process conditions.

| Process Conditions Employed in Step-I | |
|---|---|
| Temperature: | 851° C. |
| Pressure: | 1.3 atm. |
| O$_2$/natural gas ratio: | 0.09 |
| Steam/natural gas ratio: | 2.5 |
| Gas hourly space velocity (GHSV): | 3010 h$^{-1}$ |

The results obtained were as follows. The conversion of carbon in the natural gas to ethylene and oxides of carbon was 17.1% with a selectivity for ethylene of 85.6%. The composition of gaseous product stream, after removal of water vapours, was ethylene 7.5%, ethane 4.5%, methane 71.5%, propylene 0.8%, butenes 0.14%, propane 0.43%, butanes 0.1%, CO$_2$ 2.3%, CO 2.6%, and balance N$_2$, H$_2$, O$_2$, etc.

| Process Conditions Employed in Step-II | |
|---|---|
| Temperature: | 400° C. |
| Pressure: | 7.5 atm |
| Gas hourly space velocity (GHSV): | 1030 h$^{-1}$ |
| The results obtained were as follows: | |
| Total conversion of ethylene: | 96.3% |
| Selectivity for liquid hydrocarbons: | 60.2% |
| Selectivity for C$_3$ + C$_4$ hydrocarbons: | 35.6% |
| Distribution of liquid hydrocarbons | |
| C$_5$–C$_8$ paraffins (wt %): | 6.0 |
| C$_6$–C$_8$ aromatics (wt. %): | 63.5 |
| C$_9$ and C$_{10}$ hydrocarbons (wt %): | 30.5 |

EXAMPLE 4

The conversion of natural gas into liquid hydrocarbons in the two steps was carried out by the procedures described in Example 1 at the following process conditions.

| Process Conditions Employed in Step-I | |
|---|---|
| Temperature: | 947° C. |
| Pressure: | 1.1 atm. |
| O$_2$/natural gas ratio: | 0.05 |
| Steam/natural gas ratio: | 3.3 |
| Gas hourly space velocity (GHSV): | 6250 h$^{-1}$ |

The results obtained were as follows:

The conversion of carbon in natural gas to ethylene and oxides of carbon was 19.4% with a selectivity for ethylene of 95.8%. The composition of gaseous product stream, after removal of water vapours, was ethylene 9.4%, ethane 2.8%, methane 72.7%, propylenes 0.5% butenes 0.1%, propane 0.3%, butanes 0.04%, CO$_2$ 2.5%, CO 0.6%, and balance N$_2$, H$_2$, O$_2$, etc.

| Process Conditions Employed in Step-II | |
|---|---|
| Temperature: | 400° C. |
| Pressure: | 14.2 atm. |
| Gas hourly space velocity (GHSV): | 520 h$^{-1}$ |
| The results obtained were as follows: | |
| Total conversion of ethylene: | 99.5% |
| Selectivity for liquid hydrocarbons: | 52.2% |
| Selectivity for C$_3$ + C$_4$ hydrocarbons: | 45.6% |
| Distribution of Liquid Hydrocarbons | |
| C$_5$-C$_8$ paraffins (wt %): | 13.4 |
| C$_6$-C$_8$ aromatics (wt %): | 70.8 |
| C$_9$ and C$_{10}$ hydrocarbons (wt. %): | 15.8 |

EXAMPLES 5

The conversion of natural gas into liquid hydrocarbons in the two steps was carried out by the procedures described in Example 1 at the following process conditions.

| Process Conditions Employed in Step-I | |
|---|---|
| Temperature: | 705° C. |
| Pressure: | 1.8 atm. |
| O$_2$/natural gas ratio: | 0.1 |
| Steam/natural gas ratio: | 0.15 |
| Gas hourly space velocity (GHSV): | 1560 h$^{-1}$ |

The results obtained were as follows:

The conversion of carbon in natural gas to ethylene and oxides of carbon was 15.2% with a selectivity for ethylene of 65.5%. The composition of gaseous product stream, after removal of water, was ethylene 5.3%, ethane 4.6%, methane 72.2%, propylene 0.3%, butenes 0.03%, propane 0.4%, butanes 0.1%, CO$_2$ 4.1%, CO 3.3%, and balance N$_2$, H$_2$, O$_2$, etc.

| Process Conditions Employed in Step-II | |
|---|---|
| Temperature: | 500° C. |
| Pressure: | 15.1 atm |
| Gas hourly space velocity (GHSV): | 4050 h$^{-1}$ |
| The results obtained were as follows: | |
| Total conversion of ethylene: | 89.1% |
| Selectivity for liquid hydrocarbons: | 72.6% |
| Selectivity for C$_3$ + C$_4$ hydrocarbons: | 27.2% |
| Distribution of liquid hydrocarbons | |
| C$_5$-C$_8$ paraffins (wt %): | 2.8 |
| C$_6$-C$_8$ aromatics (wt %): | 92.2 |
| C$_9$ and C$_{10}$ hydrocarbons (wt. %): | 5.0 |

EXAMPLE 6

The conversion of natural gas into liquid hydrocarbons in the two steps was carried out by the procedures described in Example 1 at the following process conditions.

| Process Conditions Employed in Step-I | |
|---|---|
| Temperature: | 951° C. |
| Pressure: | 01.08 atm |
| O$_2$/natural gas ratio: | 0.05 |
| Steam/natural gas ratio: | 0.01 |
| Gas hourly space velocity (GHSV): | 1450 |

The results obtained were as follows:

The conversion of carbon in natural gas to ethylene and oxides of carbon was 23.8% with a selectivity for ethylene of 74.3%. The composition of gaseous product stream, after removal of water, was ethylene 9.1%, ethane 0.32%, methane 74.8%, propylenes 0.4%, butenes 0.1%, propane 0.2%, butanes 0.1%, CO$_2$ 3.2%, CO 5.4% and balance N$_2$, H$_2$, O$_2$, etc.

| Process Conditions Employed in Step-II | |
|---|---|
| Temperature: | 410° C. |
| Pressure: | 21.5 atm |
| Gas hourly space velocity (GHSV): | 1030 h$^{-1}$ |
| The results obtained were as follows: | |
| Total conversion of ethylene: | 99.6% |
| Selectivity for liquid hydrocarbons: | 51.3% |
| Selectivity for C$_3$ + C$_4$ hydrocarbons: | 47.4% |
| Distribution of Liquid Hydrocarbons | |
| C$_5$-C$_8$ paraffins (wt. %): | 7.5 |
| C$_6$-C$_8$ aromatics (wt %): | 90.4 |
| C$_9$ and C$_{10}$ hydrocarbons (wt %): | 2.1 |

EXAMPLE 7

The conversion of natural gas into liquid hydrocarbons in the two steps was carried out by the procedures described in Example 1 at the following process conditions.

| Process Conditions Employed in Step-I | |
|---|---|
| Temperature: | 852° C. |
| Pressure: | 1.0 atm |
| O$_2$/natural gas ratio: | 0.08 |
| Steam/natural gas ratio: | 1.8 |
| Gas hourly space velocity (GHSV): | 2290 h$^{-1}$ |

The results obtained were as follows:

The conversion of carbon in natural gas to ethylene and oxides of carbon was 19.7% with a selectivity for ethylene of 82.5%. The composition of gaseous product stream after removal of water, was ethylene 8.3%, ethane 3.5%, methane 71.3%, propylenes 0.6%, butenes 0.08%, propane 0.5%, butanes 0.05%, CO$_2$ 2.4%, CO 3.3%, and balance N$_2$, H$_2$, O$_2$, etc.

| Process Conditions Employed in Step-II | |
|---|---|
| Temperature: | 394° C. |
| Pressure: | 15.1 atm |
| Gas hourly space Velocity (GHSV): | 17130 h$^{-1}$ |
| The results obtained were as follows: | |
| Total conversion of ethylene: | 40.1% |
| Selectivity for liquid hydrocarbons: | 35.3% |
| Selectivity for C$_3$ + C$_4$ hydrocarbons: | 55.1% |
| Distribution of Liquid Hydrocarbons | |
| C$_5$-C$_8$ paraffins (wt %): | 40.2 |
| C$_6$-C$_8$ aromatics (wt %): | 53.1 |
| C$_9$ and C$_{10}$ hydrocarbons (wt. %): | 6.7 |

EXAMPLE 8

The conversion of natural gas into liquid hydrocarbons in the two steps was carried out by the procedures described in Example-1 except that the gaseous products after removal of the liquid hydrocarbons by condensation, were recycled back to the reactor of the step-I.

| Process Conditions Employed in Step-I | |
|---|---|
| Temperature: | 907° C. |
| Pressure: | 1.05 atm. |

-continued

| Process Conditions Employed in Step-I | |
|---|---|
| $O_2$/hydrocarbons ratio: | 0.12 |
| Steam/hydrocarbon ratio: | 0.05 |
| Total Gas Hourly Space Velocity (GHSV): | 660 h$^{-1}$ |

The gas hourly space velocity of the recycle gases was 420 h$^{-1}$.

The composition of gaseous product stream, after removal of water, was ethylene 7.9%, ethane 1.4%, methane 65.7%, propylenes 1.1%, butenes 0.3%, propane 0.3%, butanes 0.2%, $CO_2$ 4.4%, CO 5.8%, and balance $N_2$, $H_2$, $O_2$, etc.

| Process Conditions Employed in Step-II | |
|---|---|
| Temperature: | 400° C. |
| Pressure: | 1.7 atm. |
| Gas hourly space velocity (GHSV): | 520 h$^{-1}$ |
| The results obtained were as follows: | |
| Total conversion of ethylene: | 63.4% |
| Selectivity for liquid hydrocarbons: | 15.5% |
| Selectivity for $C_3 + C_4$ hydrocarbons: | 46.1% |
| Distribution of Liquid Hydrocarbons | |
| $C_5$-$C_8$ paraffins (wt %): | 30.5% |
| $C_6$-$C_8$ aromatics (wt. %): | 65.4% |
| $C_9$ and $C_{10}$ hydrocarbons (wt %): | 4.1% |

The gaseous products, after removal of the liquid hydrocarbons (i.e. $C_{5+}$ hydrocarbons by condensation) were recycled to the reactor of Step-I.

The main advantages of the invention are as follows:

(i) By the present two-step process, the conversion of natural gas into liquid hydrocarbons of gasoline range could be achieved in an energy-efficient manner as there is no involvement of the natural gas to syn-gas conversion step.

(ii) The product stream obtained from the first step of the present process, after removing water by condensation, is used directly as a feed for the second step, thus avoiding the high cost separation of ethylene and other olefins existing at low concentrations in the product stream of the first step. The liquid hydrocarbons formed in the second step of the present process could be separated from the product stream with ease.

(iii) The feed raw materials required in the present process are only natural gas, oxygen (or air) and steam.

(iv) There are no problems of corrosion in the process.

(v) The selectivity and yield of ethylene in the first step and of liquid hydrocarbons of gasoline range in the second step of the present process are very high.

(vi) The distribution of hydrocarbons formed in the second step viz. liquified petroleum gas ($C_3$ and $C_4$ hydrocarbons) and gasoline range liquid hydrocarbons comprising $C_5$-$C_8$ paraffins, $C_6$-$C_8$ aromatics and $C_{9+}$ hydrocarbons could be controlled by changing process conditions of the second step.

We claim:

1. A two-step process for conversion of natural gas to liquid hydrocarbons of gasoline range comprising the following consecutive steps:

1) continuously passing natural gas, steam, and at least one of either oxygen or air through a tubular reactor in the absence of a catalyst at a pressure of about 0.5–3.0 atm, a temperature of about 600°–1100° C., an $O_2$/natural gas ratio of about 0.001–0.5, a steam/natural gas ratio of about 0.001–10 and a gas hourly space velocity of about 200–50,000 h$^{-1}$ to provide an intermediate product stream, separating water from the intermediate product stream to provide a gaseous product stream comprising $C_2$-$C_4$ olefins, methane, ethane, CO, $CO_2$, propane, butane, oxygen, hydrogen, and traces of higher hydrocarbons and 2) passing the gaseous product stream from step 1) over an acid catalyst comprising platinum-containing high silica pentasil zeolite having channel diameters of 5–6 A° in a fixed bed reactor at a pressure of about 1–50 atm, a temperature of about 250°–700° C. and at a gas hourly space velocity of about 100–50,000 h$^{-1}$ to provide liquid hydrocarbons and oxides of carbon, separating the liquid hydrocarbons and oxides of carbon to provide liquid hydrocarbons in the gasoline range.

2. A two-step process as claimed in claim 1 wherein the pressure employed in the first step ranges from about 1 to 2 atm.

3. A two step process as claimed in claim 1 wherein the temperature in the first step ranges from about 700°–1000° C.

4. A two step process as claimed in claim 1 wherein the oxygen/natural gas ratio in the first step ranges from 0.003 to 0.3.

5. A two-step process as claimed in claim 1 wherein the steam/natural gas ratio in the first-step ranges from 0.01 to 5.

6. A two step process as claimed in claim 1 wherein the gas hourly space velocity in the first step ranges from 300 to 30,000 h$^{-1}$.

7. A two step process as claimed in claim 1 wherein the pressure employed in the second step ranges from 1 to 30 atm.

8. A two step process as claimed in claim 1 when the temperature in the second step ranges from 300° to 600° C.

9. A two step process as claimed in claim 1, 7 or 8 when the gas hourly space velocity in the second step ranges from 250 to 25,000 h$^{-1}$.

10. The process according to claim 1 wherein the pentasil zeolite catalyst is Pt H-ZSM-5.$Al_2O_3$.

* * * * *